United States Patent [19]

Gross

[11] 4,435,172
[45] Mar. 6, 1984

[54] ABSORBENT ARTICLE HAVING ENHANCED BLOOD ABSORPTION

[75] Inventor: James R. Gross, Lake Jackson, Tex.

[73] Assignee: The Dow Chemical Company, Midland, Mich.

[21] Appl. No.: 421,680

[22] Filed: Sep. 22, 1982

[51] Int. Cl.³ .................. D02G 3/00; A61S 13/16
[52] U.S. Cl. .................. 604/368; 428/364; 428/402; 524/168; 524/173; 524/211; 524/215; 604/375
[58] Field of Search .......... 524/168, 173, 211, 215; 428/364, 402; 604/368, 375

[56] References Cited

U.S. PATENT DOCUMENTS

| | | | |
|---|---|---|---|
| 3,997,484 | 12/1976 | Weaver et al. | 523/111 |
| 4,090,013 | 5/1978 | Ganslaw et al. | 525/329.9 |
| 4,190,563 | 2/1980 | Bosley et al. | 604/368 |

*Primary Examiner*—George F. Lesmes
*Assistant Examiner*—B. K. Johnson
*Attorney, Agent, or Firm*—B. G. Colley

[57] ABSTRACT

Absorbent articles are rendered more blood absorptive by incorporating water soluble amido compounds having the formula $$H_2N-X-NH_2$$

where X is $-CO-$, $-CS-$, $-SO-$ or $-SO_2-$, and nonionic surfactants into the articles.

13 Claims, No Drawings

ABSORBENT ARTICLE HAVING ENHANCED BLOOD ABSORPTION

BACKGROUND OF THE INVENTION

This invention relates to absorbent articles such as films, particulates, and fibers wherein the blood absorption rate is increased by the addition of amido compounds and non-ionic surfactants.

It is known from U.S. Pat. No. 4,190,563, dated Feb. 26, 1980 that water swellable absorbents can be surface treated with polyether glycols to improve the blood absorption rate. However, the present invention discloses an improvement over this patent.

SUMMARY OF THE INVENTION

It has been found that the rate of absorption of blood by water-swellable hydrophilic polymers and polyelectrolytes can be increased by the incorporation therein of water soluble amido compounds and non-ionic surfactants.

The invention is thus a water swellable hydrophilic polymer article containing an effective amount of a water soluble amido compound having the formula

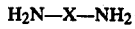

where X is —CO—, —CS—, —SO—, or —SO$_2$—, and an effective amount of a non-ionic surfactant.

The articles made herein are useful as components in sanitary towels, napkins, tampons and the like.

DETAILED DESCRIPTION OF THE INVENTION

The water-swellable or lightly crosslinked hydrophilic polymers useful in this invention can be any of the known hydrophilic polymers that are capable of being formed into a film. Examples of such polymers are disclosed in U.S. Pat. Nos. 3,997,484; 3,926,891; 3,935,099; 4,090,013; and 4,190,562.

The preferred hydrophilic polymers useful in this invention are polyelectrolytes and must be essentially water soluble in the salt form. Examples of useful polyelectrolytes include ammonium or alkali metal salts of homopolymers of acrylic or methacrylic acid and copolymers with one or more ethylenically unsaturated comonomers.

Preferably the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl groups has from 1 to 4 carbon atoms.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, 3-hydroxypropyl acrylate and 4-hydroxybutyl acrylate.

The olefinically unsaturated carboxylic acids useful in this invention are mono or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the polyacrylate to alkali metal carboxylates so that the saponified polyacrylate polymer has from 30 to 70 weight percent alkali metal carboxylates.

The partially saponified polyacrylate polymer is employed as a solution containing from 5 to 60 percent by weight of the polymer.

A list of applicable polymers which could be prepared from readily available monomers and converted into their salt form is as follows:
- acrylic acid—acrylate copolymers
- acrylic acid—acrylamide copolymers
- acrylic acid—olefinic copolymers polyacrylic acid
- acrylic acid—vinyl aromatic copolymers
- acrylic acid—styrene sulfonic acid copolymers
- acrylic acid—vinyl ether copolymers
- acrylic acid—vinyl acetate copolymers
- acrylic acid—vinyl alcohol copolymers and copolymers of methacrylic acid with all the above comonomers.

Illustrative examples of the polyfunctional crosslinking agents useful in this invention to convert the above polyelectrolytes into water-swellable polymers are set forth in U.S. Pat. Nos. 2,926,154; 3,224,986; and 3,332,901. These polyfunctional crosslinking agents are generally known as polyamide-polyamine epichlorohydrin adducts. The disclosures of these references are incorporated herein by reference. Similar crosslinking agents are also commercially available from Hercules Incorporated as Kymene 557 and Polycup 172. The structure of these adducts has been discussed in an article by M. E. Corr, et al Journal of Applied Polymer Science, Vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as eipchlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380 bisphenol A-epichlorohydrin epoxy resins having an epoxy equivalent weight range from about 182 to about 975 and mixtures of the foregoing.

Also useful as crosslinking agents are monomeric amine-epihalohydrin adducts prepared by reacting at least two moles of an epihalohydrin with one mole of various monoamines, diamines and triamines at a temperature in the range from 0° to 90° C. for a time period of 0.5 to 8 hours. The reaction is carried out in a reaction media containing 20 to 90 percent water, lower alcohols such as methanol or ethanol, or in aqueous solutions of the lower alcohols. The amine-epihalohydrin adducts are used directly as made without separation of concentration. The preparation and use of amino-epihalohydrin adducts as crosslinking agents is further disclosed in the patent by J. R. Gross, U.S. Pat. No. 4,310,593. This patent is incorporated by reference herein.

Sulfonium zwitterions are known from U.S. Pat. Nos. 3,660,431, 3,749,737 and 3,749,738. The disclosures of these patents are incorporated herein by reference.

These crosslinking agents are used in an amount from about 0.05 to about 5.0% based on the weight of the polyelectrolyte used. This is generally sufficient to cause the polyelectrolyte to become lightly crosslinked.

For the purpose of this invention an effective amount of the amido compounds is 2 to 20 percent by weight based on the weight of the polyelectrolyte and an effective amount of the non-ionic surfactant is 2 to 15 percent by weight.

Examples of useful amido compounds that can be used herein are urea ($H_2N-CO-NH_2$) thiorea, ($H_2N-CS-NH_2$) thionamide, ($H_2N-SO-NH_2$) and sulfamide ($H_2N-SO_2-NH_2$).

Examples of useful non-ionic surfactants are sorbitan fatty acid esters having 12 to 18 carbon atoms in the acid moiety, ethoxylated aliphatic alcohols having 12 to 18 carbon atoms in the alcohol moiety and 1 to 20 moles of ethylene oxide combined therein, polyoxyethylene fatty acid esters having 12 to 18 carbon atoms in the acid moiety and 10 to 40 moles of ethylene oxide combined therein, and polyoxypropylene polyoxyethylene copolymers containing 20 to 90 percent by weight of polyoxyethylene groups. These surfactants are well known from the Encyclopedia of Chemical Technology, Second Edition (1969) Volume 19, pages 531–554. This article is incorporated by reference herein.

The following examples are presented to illustrate the invention further and are not to be considered a limitation on the scope of the invention.

Three mixtures were made up having the following composition:

| Part A | Part B | Part C |
|---|---|---|
| 600 g deionized water | 437.5 g ethyl acrylate | 175 g deionized water |
| 0.75 g Triton GR-5* | 77.2 g methacrylic acid | 2.0 g sodium bisulfite |
| 1.75 g sodium persulfate | | |

*dioctylsodium sulfosuccinate

Part A was charged to a 2 liter reactor and brought to 40° C. while under vigorous nitrogen purge. Eighteen milliliters of Part B was added to the reactor followed by all Part C. The remainder of Part B was added over the next 2.5 hours while the temperature was held at 39°–40° C. The latex was then digested at 60° C. for 1.5 hours, cooled to 30° C. and bottled. The latex contained 40.6% non-volatiles.

1125 g of the above latex was added in a small stream over a period of 25 minutes to a slowly stirred solution of 187.16 g 50% NaOH in 547.9 g. deionized water. After the polymer had all dissolved, the viscous solution was heated at 50° C. for 22 hours to complete the saponification. The resulting solution (25.4% solids) had a Brookfield viscosity of 16,200 cps at 25° C. (No 5 spindle, 10 r.p.m.). The polymer is 50% ethylacrylate by moles with the remainder being sodium acrylate and methacrylate.

A 25% polyelectrolyte solution (prepared as above was blended with a curing agent (Hercules' Polycup 172) at the active level of 1% based on the polymer and then any other additives and sufficient water to dilute all samples in a series to the same polymer concentration. The solution is spread on a Teflon sheet using a 30-mil draw bar and the sheet is placed in a 125° C. circulating air oven for 30 minutes. The films are checked for absorption rate when right out of the oven and again after several hours at 60% relative humidity in the room. The absorption rate is defined as the time in seconds for a drop of heparinized pig blood gently placed on the horizontal supported film to sink even with the surface of the film. A bottle cap was used as a support for the film sample.

Control A—5% non-ionic surfactant based on the polyelectrolyte.

10.0 grams of a 25% solution of acrylic polyelectrolyte, prepared as set forth above is mixed with 5 g water, 0.125 g sorbitan monolaurate (Tween 20 by Atlas Chemical) and 0.2 g of 12.5% crosslinker (Polycup 172 by Hercules). A 30-mil wet film is cast on Teflon and baked for 30 minutes in a 125° C. circulating air oven.

Control B—No surfactant

Prepared as in Control A except no non-ionic surfactant added.

Control C—5% non-ionic surfactant

Prepared as in Control A except 7.5 g water added.

Control D—10% urea

Prepared as in Control B except 5 g of 5% aqueous urea added in place of the 5 g water.

EXAMPLE 1

10% urea and 5% non-ionic surfactant
Prepared as in Control A except 5 g of 5% aqueous urea added in place of the 5 g water.

EXAMPLE 2

2.5% urea+5% surfactant
Prepared as in Control C only 1.25 g of 5% aqueous urea and 6.25 g water replaced the 7.5 g water.

EXAMPLE 3

5% urea+5% surfactant
Prepared as in Control C only 2.5 g of 5% aqueous urea and 5 g water replaced the 7.5 g water.

EXAMPLE 4

10% urea+5% surfactant
Prepared as in Control C only 5 g of 5% aqueous urea and 2.5 g water.

EXAMPLE 5

15% urea+5% surfactant
Prepared as in Control C only 7.5 g of 5% aqueous urea replaced the 7.5 g water.

TABLE I

| Blood Absorption Rate of Absorbent Polymer Films | | |
|---|---|---|
| Film Sample | Dry Film Rate (Seconds) | Film Rate at 60% R.H. (seconds) |
| Control A | 300 | 145 |
| Control B | >1800 | 368 |
| Control C | 444 | 287 |

TABLE I-continued

| | Blood Absorption Rate of Absorbent Polymer Films | |
|---|---|---|
| Film Sample | Dry Film Rate (Seconds) | Film Rate at 60% R.H. (seconds) |
| Control D | 420 | 375 |
| Example 1 | 180 | 46 |
| Example 2 | 217 | 136 |
| Example 3 | 166 | 81 |
| Example 4 | 126 | 86 |
| Example 5 | 155 | 79 |

As shown by Examples 1-5, there is a surprising synergism when urea is added to a formulation already containing non-ionic surfactant.

I claim:

1. A water-swellable hydrophilic polymer article containing an effective amount of a water soluble amido compound having the formula $$H_2N-X-NH_2$$

where X is —CO—, —CS—, —SO— or —SO$_2$—, and an effective amount of a non-ionic surfactant which are effective to improve the blood absorption rate of said article.

2. The article of claim 1 wherein the article is a film.

3. The article of claim 1 wherein the article is a fiber.

4. The article of claim 1 wherein the article is a particulate.

5. The article of claim 1 wherein the non-ionic surfactant is selected from the group consisting of sorbitan fatty acid esters having 12 to 18 carbons in the acid moiety; ethoxylated aliphatic alcohols having 12 to 18 carbons in the alcohol moiety and 1 to 20 moles of ethylene oxide combined therein; polyoxyethylene fatty acid esters having 12 to 18 carbons in the acid moiety and 10 to 40 moles of ethylene oxide combined therein; and polyoxypropylene polyoxyethylene copolymers containing 20 to 90 percent by weight of polyoxyethylene groups.

6. The article of claim 1 wherein the percent by weight of said amido compound based on said polyelectrolyte is in the range from 2 to 20% and the percent by weight of said non-ionic surfactant based on said polyelectrolyte is in the range from 2 to 15%.

7. The article of claim 1 where the amido compound is urea and the non-ionic surfactant is sorbitan monolaurate.

8. A water swellable polyelectrolyte article containing an amount of urea and an sorbitan fatty acid ester having 12 to 18 carbons in the acid moiety which are effective to improve the blood absorption rate of said article.

9. The article of claim 8 wherein the article is a film.

10. The article of claim 8 wherein the article is a fiber.

11. The article of claim 8 wherein the article is a particulate.

12. The article of claim 8 wherein said sorbitan ester surfactant is sorbitan monolaurate.

13. The article of claim 8 wherein the percent by weight of urea based on said polyelectrolyte is in the range from 5 to 10% and the percent by weight of said sorbitan ester based on said polyelectrolyte is in the range from 5 to 10%.

* * * * *

UNITED STATES PATENT AND TRADEMARK OFFICE
CERTIFICATE OF CORRECTION

PATENT NO. : 4,435,172
DATED : March 6, 1984
INVENTOR(S) : James R. Gross

It is certified that error appears in the above—identified patent and that said Letters Patent is hereby corrected as shown below:

Col. 3, line 20, "thiorea" should be --thiourea--.

In Claim 1, line 1 Col. 5; delete the entire line and insert --An absorbent article comprising a water swellable hydrophilic polymer" and line 2 delete "containing" and insert --having incorporated therein".

In Claim 6, line 2, Col. 6; delete "polyelectrolyte" and insert -- hydrophilic polymer--.

In Claim 8, line 1, Col. 6; delete the entire line and insert --An absorbent article comprising a water swellable polyelectrolyte--; line 2 delete "containing an" and insert --having incorporated therein an effective--.

Signed and Sealed this

Seventh Day of August 1984

[SEAL]

Attest:

GERALD J. MOSSINGHOFF

Attesting Officer     Commissioner of Patents and Trademarks